US00PP18088P2

(12) United States Plant Patent
Heffner

(10) Patent No.: US PP18,088 P2
(45) Date of Patent: Sep. 25, 2007

(54) ***IMPATIENS* PLANT NAMED 'BODLIZVIOSTA'**

(50) Latin Name: *Impatiens walleriana*
Varietal Denomination: Bodlizviosta

(75) Inventor: Michael Heffner, Santa Barbara, CA (US)

(73) Assignee: John Bodger + Sons Company, South EL Monte, GA (US)

( * ) Notice: Subject to any disclaimer, the term of this patent is extended or adjusted under 35 U.S.C. 154(b) by 0 days.

(21) Appl. No.: 11/415,476

(22) Filed: May 1, 2006

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—C. A. Whealy

(57) ABSTRACT

A new and distinct cultivar of Mini *Impatiens* plant named 'Bodlizviosta', characterized by its compact, upright, outwardly spreading and mounded plant habit; freely branching habit; dense and bushy growth habit; small dark green-colored leaves; freely flowering habit; and red purple and white bi-colored flowers that are positioned above and beyond the foliage.

1 Drawing Sheet

Botanical designation: *Impatiens walleriana.*
Cultivar denomination: 'Bodlizviosta'.

BACKGROUND OF THE INVENTION

The present invention relates to a new and distinct cultivar of Mini *Impatiens* plant, botanically known as *Impatiens walleriana,* and hereinafter referred to by the name 'Bodlizviosta'.

The new Mini *Impatiens* is a product of a planned breeding program conducted by the Inventor in Lompoc, Calif. The objective of the breeding program was to develop new compact and freely-branching Mini *Impatiens* cultivars with numerous flowers and attractive foliage and flower coloration.

The new Mini *Impatiens* originated from a self-pollination made by the Inventor in June, 2002, of a proprietary selection of *Impatiens walleriana* identified as code number 2IM388-1, not patented. The cultivar Bodlizviosta was discovered and selected by the Inventor as a flowering plant within the progeny of the stated self-pollination in a controlled environment in Lompoc, Calif. in January, 2003.

Asexual reproduction of the new cultivar by terminal cuttings propagated in a controlled environment in Lompoc, Calif. has shown that the unique features of this new Mini *Impatiens* are stable and reproduced true to type in successive generations of asexual reproduction.

SUMMARY OF THE INVENTION

The cultivar Bodlizviosta has not been observed under all possible environmental conditions. The phenotype may vary somewhat with variations in environment such as temperature and light intensity, without, however, any variance in genotype.

The following traits have been repeatedly observed and are determined to be the unique characteristics of 'Bodlizviosta'. These characteristics in combination distinguish 'Bodlizviosta' as a new and distinct cultivar of Mini *Impatiens:*

1. Compact, upright, outwardly spreading and mounded plant habit.
2. Freely branching habit; dense and bushy growth habit.
3. Small dark green-colored leaves.
4. Freely flowering habit.
5. Red purple and white bi-colored flowers that are positioned above and beyond the foliage.

In side-by-side comparisons conducted in Lompoc, Calif., plants of the new Mini *Impatiens* differed from plants of the parent selection in the following characteristics:

1. Plants of the new Mini *Impatiens* had smaller leaves than plants of the parent selection.
2. Plants of the new Mini *Impatiens* had smaller flowers than plants of the parent selection.
3. Plants of the new Mini *Impatiens* have red purple and white bi-colored flowers whereas plants of the parent selection have solid red purple-colored flowers.

Plants of the new Mini *Impatiens* can be compared to plants of the Mini *Impatiens* cultivar Bodlizvio, disclosed in U.S. Plant Pat. No. 15,198. In side-by-side comparisons conducted in Lompoc, Calif. ,plants of the new Mini *Impatiens* differed from plants of the cultivar Bodlizvio primarily in flower coloration as plants of the cultivar Bodlizorg had solid red purple-colored flowers.

BRIEF DESCRIPTION OF THE PHOTOGRAPHS

The accompanying photographs illustrate the overall appearance of the new Mini *Impatiens.* These photographs show the colors as true as it is reasonably possible to obtain in colored reproductions of this type. Colors in the photographs may differ slightly from the color values cited in the detailed botanical description which accurately describe the colors of the new Mini *Impatiens.*

The photograph at the bottom of sheet comprises a side perspective view of a typical flowering plant of 'Bodlizviosta' grown in a container.

The photograph at the top of the sheet comprises a close-up view of typical flowers of 'Bodlizviosta'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lompoc, Calif. during the winter and spring in a polycarbonate-covered greenhouse and under conditions and practices which approximate those generally used in commercial Mini *Impatiens* production. During the production of the plants, day temperatures ranged from about 21° C. to 24° C., night temperatures ranged from about 16° C. to 18° C. and light levels ranged from about 4,000 foot-candles to 8,000 foot-candles. Measurements and numerical values represent averages for typical flowering plants. Single plants were grown in 15-cm pots and were about 19 weeks old when the photographs and the detailed description were taken.

Botanical classification: *Impatiens walleriana* cultivar Bodlizviosta.

Parentage: Self-pollination of a proprietary selection of *Impatiens walleriana* identified as code number 2IM388-1, not patented.

Propagation:

*Type.*—Terminal cuttings.

*Time to initiate roots.*—About two weeks at 22° C.

*Time to produce a rooted young plant.*—About four weeks at 20° C.

*Root description.*—Fine, fibrous; white in color.

*Rooting habit.*—Freely branching.

Plant description:

*Plant form.*—Compact, upright, outwardly spreading and mounded plant habit.

*Growth and branching habit.*—Moderately vigorous and freely-branching growth habit with about 20 basal branches; secondary and tertiary branches forming potentially at every node; dense and bushy growth habit. Pinching, that is removal of the terminal apex, is typically not required, but will enhance branching.

*Plant height.*—About 16 cm.

*Plant diameter or spread.*—About 42 cm.

*Lateral branches.*—Length: About 18 cm. Diameter: About 5 mm. Internode length: About 1.1 cm. Texture: Smooth, glabrous. Color: 144A with random flecks, 183A.

Foliage description:

*Arrangement.*—Alternate, simple.

*Length.*—About 3.6 cm.

*Width.*—About 2 cm.

*Shape.*—Elliptical.

*Apex.*—Acute.

*Base.*—Attenuate.

*Margin.*—Slightly crenate with ciliation.

*Texture, upper and lower surfaces.*—Smooth, glabrous.

*Venation pattern.*—Pinnate.

*Color.*—Developing and fully expanded foliage, upper surface: 147A. Developing and fully expanded foliage, lower surface: 147B. Venation, upper and lower surfaces: 147B.

*Petiole.*—Length: About 2.4 cm. Diameter: About 2 mm. Texture, upper and lower surfaces: Smooth, glabrous. Color, upper and lower surfaces: 144D.

Flower description:

*Flower type and habit.*—Numerous single star-shaped flowers. About three flowers arranged in axillary clusters. Freely flowering, usually about 54 flowers and flower buds per lateral branch. Flowers positioned above the foliage and typically face upright or outward. Flowers last about five to seven days under greenhouse conditions. Flowers not persistent. Flowers not fragrant.

*Natural flowering season.*—Flowering is continuous through the spring and summer.

*Flower size.*—Height: About 3 cm. Width: About 3 cm. Depth (not including spur): About 2 cm.

*Flower buds.*—Length: About 1 cm. Diameter: About 6 mm. Shape: Ovoid. Color: 78A.

*Petals.*—Quantity/arrangement: Five per flower in a single whorl. Length, banner petal: About 1.4 cm. Length, lateral petals: About 1.6 cm. Length, basal petals: About 1.8 cm. Width, banner petal: About 1.5 cm. Width, lateral petals: About 1 cm. Width, basal petals: About 1 cm. Shape: Obovate to slightly cordate. Apex: Rounded and slightly emarginate. Base: Acute. Margin: Entire. Texture, upper and lower surfaces: Smooth, glabrous. Color: When opening, upper surface: Towards the margins, 74A; towards the centers, 155D. When opening, lower surface: 71C. Fully opened, upper surface: Towards the margins, 74A; towards the centers, 75A; towards the base, 155D. Red purple color becoming closer to 75A with development. Fully opened, lower surface: Towards the margins, 71C; central stripe, 155D.

*Sepals.*—Quantity/arrangement: Five in a single whorl; one modified into an elongated spur. Calyx length: About 5 mm. Calyx diameter: About 5 mm. Shape: Elliptic. Apex: Acute. Margin: Entire. Texture, upper and lower surfaces: Smooth, glabrous. Color, upper and lower surfaces: Close to 144A. Spur length: About 2.7 cm. Spur diameter: At flower, about 2 mm; at apex, less than 1 mm. Spur color: 157C.

*Peduncles.*—Length: About 1.7 cm. Diameter: About 2 mm. Angle: About 45° from vertical. Strength: Strong. Texture: Smooth, glabrous. Color: 144C.

*Reproductive organs.*—Stamens: Quantity: Five fused around stigma. Anther length: About 2 mm. Anther color: 75C. Pollen amount: Scarce. Pollen color: 77C. Pistils: Quantity per flower: One. Pistil length: About 4 mm. Stigma shape: Rounded. Stigma color: 157A. Style color: 147A. Ovary color: 147A.

*Seed/fruit.*—Seed and fruit production have not been observed.

Disease/pest resistance: Plants of the new *Impatiens* have not been observed to be resistant to pathogens and pests common to *Impatiens*.

It is claimed:

1. A new and distinct Mini *Impatiens* plant named 'Bodlizviosta' as illustrated and described.

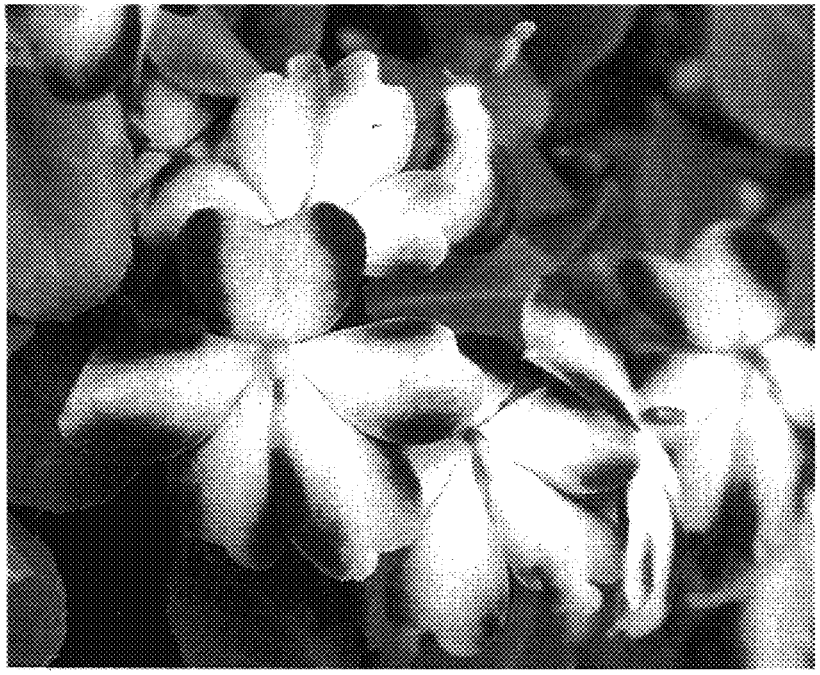
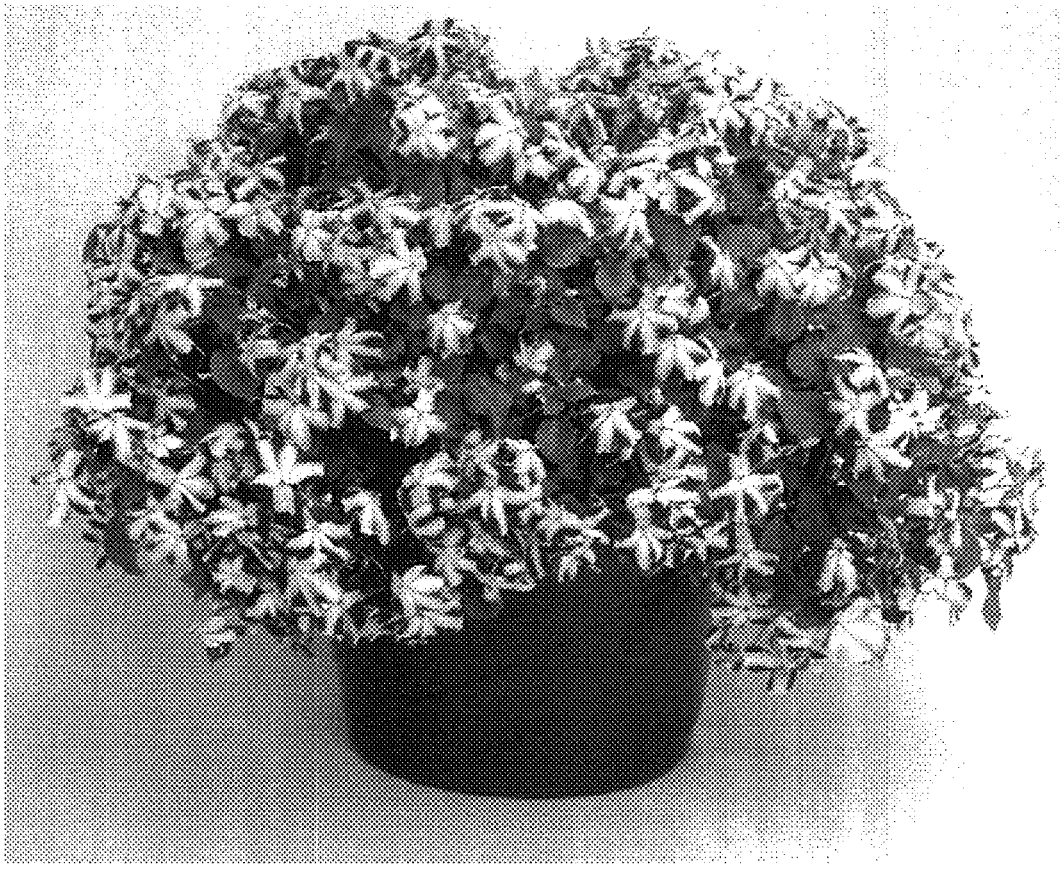

* * * * *